US010632275B2

(12) United States Patent
Wong et al.

(10) Patent No.: US 10,632,275 B2
(45) Date of Patent: Apr. 28, 2020

(54) HEADGEAR COMPRISING SPACER FABRIC

(71) Applicant: ResMed Pty Ltd, Bella Vista, New South Wales (AU)

(72) Inventors: Chiew Khuen Wong, Sydney (AU); Kirrily Michele Haskard, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 311 days.

(21) Appl. No.: 15/510,792

(22) PCT Filed: Sep. 15, 2015

(86) PCT No.: PCT/AU2015/050546
§ 371 (c)(1),
(2) Date: Mar. 13, 2017

(87) PCT Pub. No.: WO2016/041008
PCT Pub. Date: Mar. 24, 2016

(65) Prior Publication Data
US 2017/0259022 A1   Sep. 14, 2017

(30) Foreign Application Priority Data

Sep. 16, 2014  (AU) ................................ 2014903687

(51) Int. Cl.
*A61M 16/06* (2006.01)
(52) U.S. Cl.
CPC ........ *A61M 16/0683* (2013.01); *A61M 16/06* (2013.01); *A61M 16/0616* (2014.02); *A61M 16/0666* (2013.01); *A61M 2205/02* (2013.01)
(58) Field of Classification Search
CPC ............................................... A61M 16/0683

USPC .......................................................... 442/312
See application file for complete search history.

(56) References Cited

U.S. PATENT DOCUMENTS

| 4,782,832 | A  | 11/1988 | Trimble et al. |
| 4,944,310 | A  | 7/1990  | Sullivan |
| 6,532,959 | B1 | 3/2003  | Berthon-Jones |
| 6,581,594 | B1 | 6/2003  | Drew et al. |
| 7,497,097 | B2 | 3/2009  | Herr |
| 7,866,944 | B2 | 1/2011  | Kenyon et al. |
| 8,636,479 | B2 | 1/2014  | Kenyon et al. |
| 8,638,014 | B2 | 1/2014  | Sears et al. |

(Continued)

FOREIGN PATENT DOCUMENTS

| CN | 103906545      | 7/2014 |
| WO | WO 98/004310 A1 | 2/1998 |

(Continued)

OTHER PUBLICATIONS

Apr. 5, 2018 Extended European Search Report issued in European Application No. 15842627.0.

(Continued)

*Primary Examiner* — Jenna L Johnson
(74) *Attorney, Agent, or Firm* — Nixon & Vanderhye P.C.

(57) ABSTRACT

A positioning and stabilising structure for a patient interface for delivery of a supply of pressurized air or breathable gas to a patient's airways may include a first fabric layer; a second fabric layer; a central fabric layer between the first fabric layer and the second fabric layer. The central fabric layer, the first fabric and the second fabric may be warp/weft knitted together.

18 Claims, 16 Drawing Sheets

(56) References Cited

U.S. PATENT DOCUMENTS

| | | |
|---|---|---|
| 8,733,349 B2 | 5/2014 | Bath et al. |
| 2009/0044808 A1 | 2/2009 | Guney et al. |
| 2009/0050156 A1 | 2/2009 | Ng et al. |
| 2010/0000534 A1 | 1/2010 | Kooij et al. |
| 2010/0000544 A1 | 1/2010 | Blasczykiewicz et al. |
| 2011/0197341 A1 | 8/2011 | Formica et al. |
| 2012/0138060 A1 | 6/2012 | Barlow |
| 2013/0220327 A1 | 8/2013 | Barlow et al. |
| 2014/0209098 A1 | 7/2014 | Dunn et al. |

FOREIGN PATENT DOCUMENTS

| | | |
|---|---|---|
| WO | WO 98/034665 A1 | 8/1998 |
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/107858 A1 | 8/2012 |
| WO | WO 2012/171072 A1 | 12/2012 |
| WO | WO 2013/020167 A1 | 2/2013 |
| WO | WO 2013/026091 A1 | 2/2013 |
| WO | WO-2013026091 A1 * | 2/2013 ........ A61M 16/0683 |

OTHER PUBLICATIONS

International Search Report for PCT/AU2015/050546, dated Dec. 2, 2015, 4 pages.
Written Opinion of the ISA for PCT/AU2015/050546, dated Dec. 2, 2015, 5 pages.
"*Respiratory Physiology*", by John B. West, Lippincott Williams & Wilkins, 9$^{th}$ edition published 2012 (8 pages).
Chinese Office Action and its English translation for Chinese Application No. 201580049256.4, 15 pages, dated Dec. 21, 2018.
Japanese Office Action dated May 20, 2019 in corresponding Japanese Application No. 2017-514898, and English translation thereof, 20 pages.

* cited by examiner

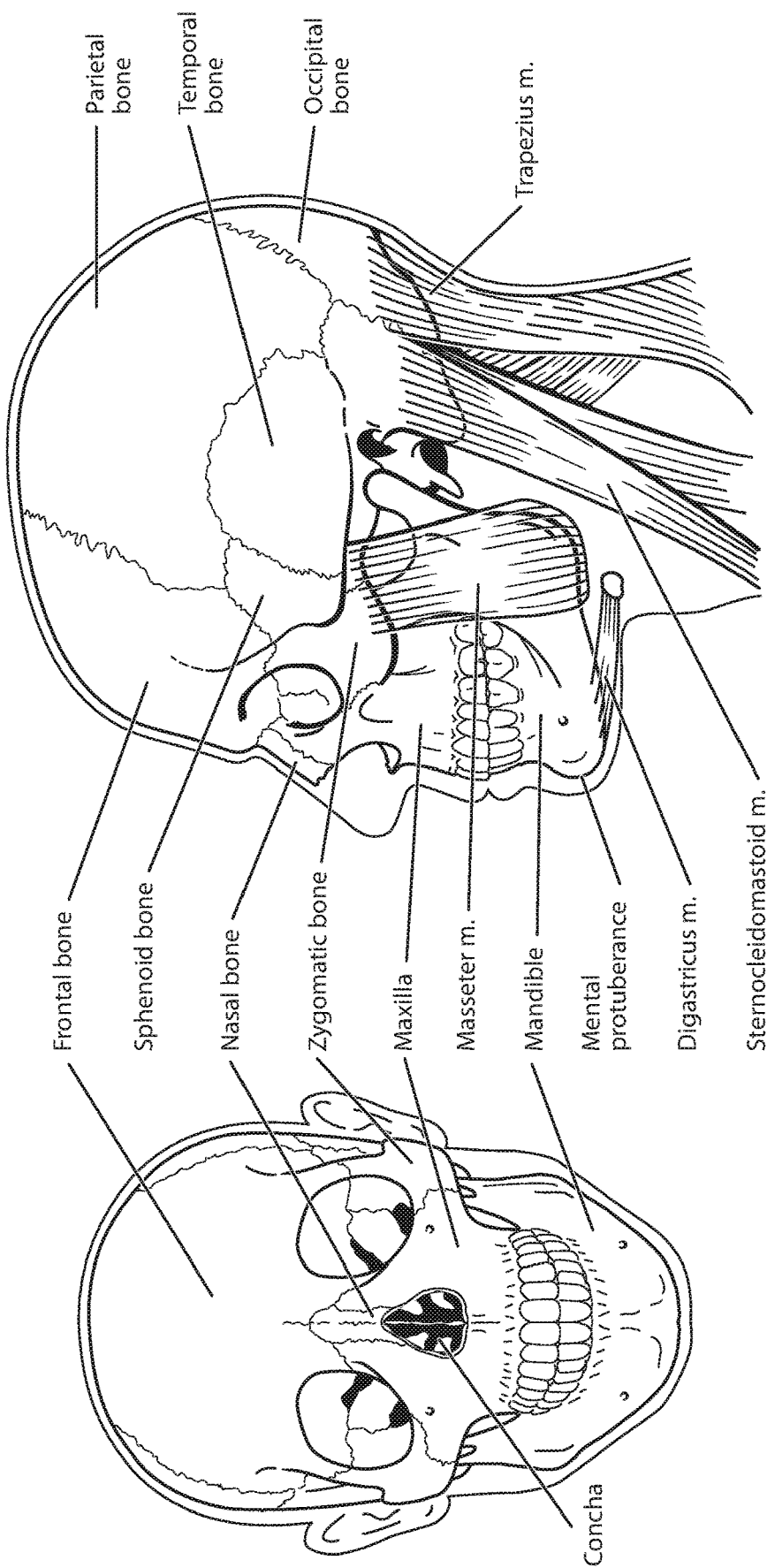

Relatively Large Positive Curvature

Relatively Small Positive Curvature

Zero Curvature

Relatively Small Negative Curvature

Relatively Large Negative Curvature

HEADGEAR COMPRISING SPACER FABRIC

This application is the U.S. national phase of International Application No. PCT/AU2015/050546 filed 15 Sep. 2015, which designated the U.S. and claims priority to AU Provisional Application. No 2014903687, filed 16 Sep. 2014, the entire contents of each of which are hereby incorporated by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

This application claims the benefit of AU Provisional Application. No 2014903687, filed 16 Sep. 2014.

BACKGROUND OF THE TECHNOLOGY

Field of the Technology

The present technology relates to one or more of the detection, diagnosis, treatment, prevention and amelioration of respiratory-related disorders. The present technology also relates to medical devices or apparatus, and their use.

Description of the Related Art

Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

Therapy

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the patient's face when force is applied to the patient interface with the seal-forming portion in confronting engagement with the patient's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris, however some patients find these uncomfortable.

Another form of seal-forming portion may use adhesive to achieve a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063, 328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use. The material used to form the straps and/or stabilising harnesses may contribute to these problems.

Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient. The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

One form of the present technology comprises a positioning and stabilising structure for a patient interface for delivery of a supply of pressurized air or breathable gas to a patient's airways, the positioning and stabilising structure comprising: a first fabric layer; a second fabric layer; a central fabric layer between the first fabric layer and the second fabric layer, wherein the central fabric layer, the first fabric and the second fabric are warp/weft knitted together.

In examples, (a) the central fabric layer, the first fabric layer and the second fabric layer form a strap of the positioning and stabilising structure;

(b) the strap is porous;
(c) the strap is elastic at least along a length of the strap;
(d) the strap does not comprise foam;
(e) the first fabric layer, the second fabric layer and the central fabric layer are made by warp knitting;
(f) the central fabric layer is made by a 3D knitting machine;
(g) the central fabric layer, the first fabric layer and the second fabric layer together are 2.0 mm to 6.0 mm thick;
(h) the central fabric layer, the first fabric layer and the second fabric layer together are 4.0 mm to 6.0 mm thick;
(i) the central fabric layer, the first fabric layer and the second fabric layer together are 2.0 mm to 4.0 mm thick;
(j) the central fabric layer, the first fabric layer and the second fabric layer together have a compression strength that is 15 kilopascals to 25 kilopascals;
(k) the central fabric layer, the first fabric layer and the second fabric layer together have 0.1% to 5% elongation when a 10 Newtons force is applied;
(l) the central fabric layer, the first fabric layer and the second fabric layer together have 10% to 20% elongation when a 10 Newtons force is applied;
(m) the central fabric layer, the first fabric layer and the second fabric layer together have 10% to 15% elongation when a 10 Newtons force is applied;
(n) the central fabric layer, the first fabric layer and the second fabric layer together have 10% to 30% elongation when a 2 Newtons force is applied;
(o) the central fabric layer is a yarn layer;
(p) yarn of the yarn layer comprises cotton;
(q) yarn of the yarn layer comprises polyester;
(r) the yarn layer comprises a predetermined number of yarns per square centimetre to provide a predetermined amount of elasticity and flexibility to the positioning and stabilising structure;
(s) wherein the yarns of the yarn layer have a predetermined thickness and/or predetermined height to provide a predetermined amount of elasticity and flexibility to the positioning and stabilising structure;
(t) the central fabric layer, the first fabric layer and the second fabric layer are not flame laminated together or are not glue laminated together;
(u) the positioning and stabilising structure further comprises a rigidiser arm inserted into the central fabric layer pushing fibres out of the way, wherein the rigidiser arm is configured to guide a headgear vector when the positioning and stabilising structure is stretched;
(v) the headgear vector is between the patient's eyes and ears;
(w) the positioning and stabilising structure further comprises at least one rigidising element within the central fabric layer to prevent stretching of the positioning and stabilising structure;
(x) the positioning and stabilising structure does not comprise foam;
(y) the first fabric layer is a mesh or open surface or pattern;
(z) the first fabric layer has at least one exposed portion exposing the central fabric layer;
(aa) the positioning and stabilising structure further comprises a third fabric layer on the second fabric layer such that the second fabric layer is between the central fabric layer and the third fabric layer, wherein the third fabric layer is configured to fasten to hooks of a hook and loop fastener to enable length adjustment of the positioning and stabilising structure;
(bb) the positioning and stabilising structure is folded to adjust a length of the positioning and stabilising structure;
(cc) the third fabric layer is an unbroken loop material;
(dd) the third fabric layer comprises loops of the hook and loop fastener;
(ee) the hooks of the hook and loop fastener are provided on a distal or free end of a strap;
(ff) the central fabric layer, the first fabric layer and the second fabric layer together have 6% to 10% elongation when a 10 Newtons force is applied;
(gg) the positioning and stabilising structure further comprises a third fabric layer, a fourth fabric layer, a second central fabric layer between the third fabric layer and the fourth fabric layer, wherein the second central fabric layer, the third fabric layer and the fourth fabric layer are warp/weft knitted together, the central fabric layer, the first fabric layer and the second fabric layer form a first strap portion of the positioning and stabilising structure, and the second central fabric layer, the third fabric layer and the fourth fabric layer form a second strap portion of the positioning and stabilising structure;
(hh) the second fabric layer and the fourth fabric layer are the same material;
(ii) the first strap portion and the second strap portion have different elongations when an identical force is applied to the first strap portion and the second strap portion;
(jj) the positioning and stabilising structure further comprises a fifth fabric layer, a sixth fabric layer, a third central fabric layer between the fifth fabric layer and the sixth fabric layer, wherein the third central fabric layer, the fifth fabric layer and the sixth fabric layer are warp/weft knitted together, the central fabric layer, the first fabric layer and the second fabric layer form a first strap portion of the positioning and stabilising structure, the third central fabric layer, the fifth fabric layer and the sixth fabric layer form a third strap portion of the positioning and stabilising structure, and the first strap portion, the second strap portion and the third strap portions have different elongations when an identical force is applied to the first strap portion, the second strap portion and the third strap portion; and/or
(kk) the first fabric layer, the second fabric layer and the central fabric layer together form a 3D spacer fabric.

One form of the present technology comprises a method of manufacturing a positioning and stabilising structure for a patient interface for delivery of a supply of pressurized air or breathable gas to a patient's airways, the method comprising: warp/weft knitting together a first fabric layer, a second fabric layer and a central fabric layer between the first fabric layer and the second fabric layer to form multilayered fabric, and forming the multilayered fabric into headgear of the positioning and stabilising structure.

In examples, (a) the multilayered fabric is formed into at least one strap for the headgear; and/or (b) the headgear is formed by cutting the multilayered fabric into a desired shape.

One form of the present technology comprises a patient interface for sealed delivery of a flow of air at a continuously positive pressure with respect to ambient air pressure to an entrance to the patient's airways including at least entrance of a patient's nares, wherein the patient interface is configured to maintain a therapy pressure in a range of about 4 cmH$_2$O to about 30 cmH$_2$O above ambient air pressure in use, throughout the patient's respiratory cycle, while the patient is sleeping, to ameliorate sleep disordered breathing; said patient interface comprising: a sealing structure configured to form a seal around the entrance to the patient's airways; a plenum chamber pressurised at a pressure above ambient pressure in use; a gas washout vent configured to allow a flow of patient exhaled $CO_2$ to an exterior of the patient interface to minimise rebreathing of exhaled $CO_2$ by the patient; and a positioning and stabilising structure comprising a first fabric layer, a second fabric layer, and a central fabric layer between the first fabric layer and the second fabric layer, wherein the central fabric layer, the first fabric and the second fabric are warp/weft knitted together.

Another form of the present technology comprises a positioning and stabilising structure for a patient interface for delivery of a supply of pressurized air or breathable gas to a patient's airways, the positioning and stabilising structure comprising: a first fabric layer; a second fabric layer; and a central fabric layer between the first fabric layer and the second fabric layer, wherein the central fabric layer, the first fabric and the second fabric are knit to shape.

An aspect of certain forms of the present technology is a medical device that is easy to use, e.g. by a person who does not have medical training, by a person who has limited dexterity or vision or by a person with limited experience in using this type of medical device.

An aspect of one form of the present technology is a positioning and stabilising structure that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE DRAWINGS

The present technology is illustrated by way of example, and not by way of limitation, in the figures of the accompanying drawings, in which like reference numerals refer to similar elements including.

Treatment Systems

Respiratory System and Facial Anatomy

Figure 1A:
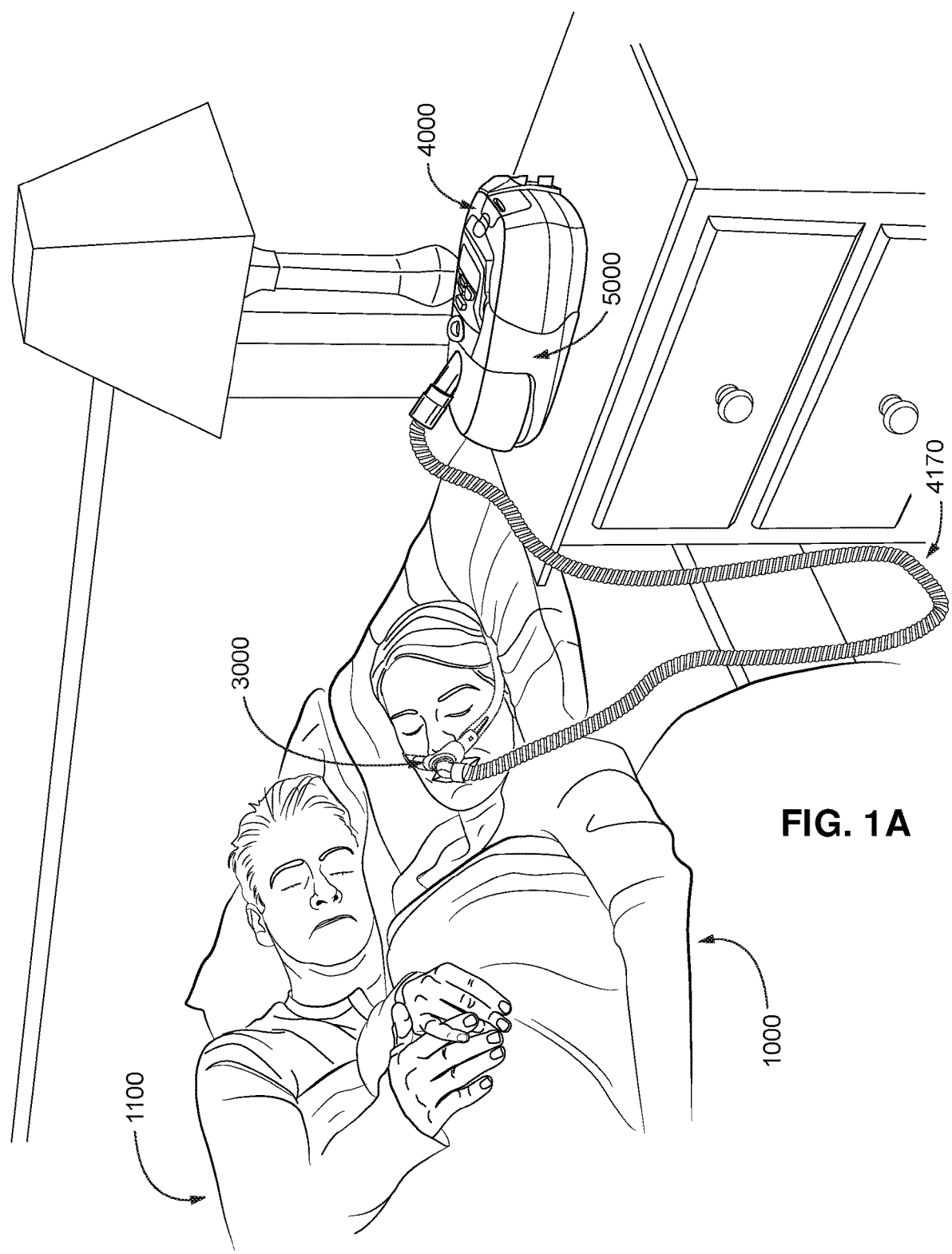
FIG. 1A shows a system including a patient 1000 wearing a patient interface 3000, in the form of a nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown.
Figure 1B:
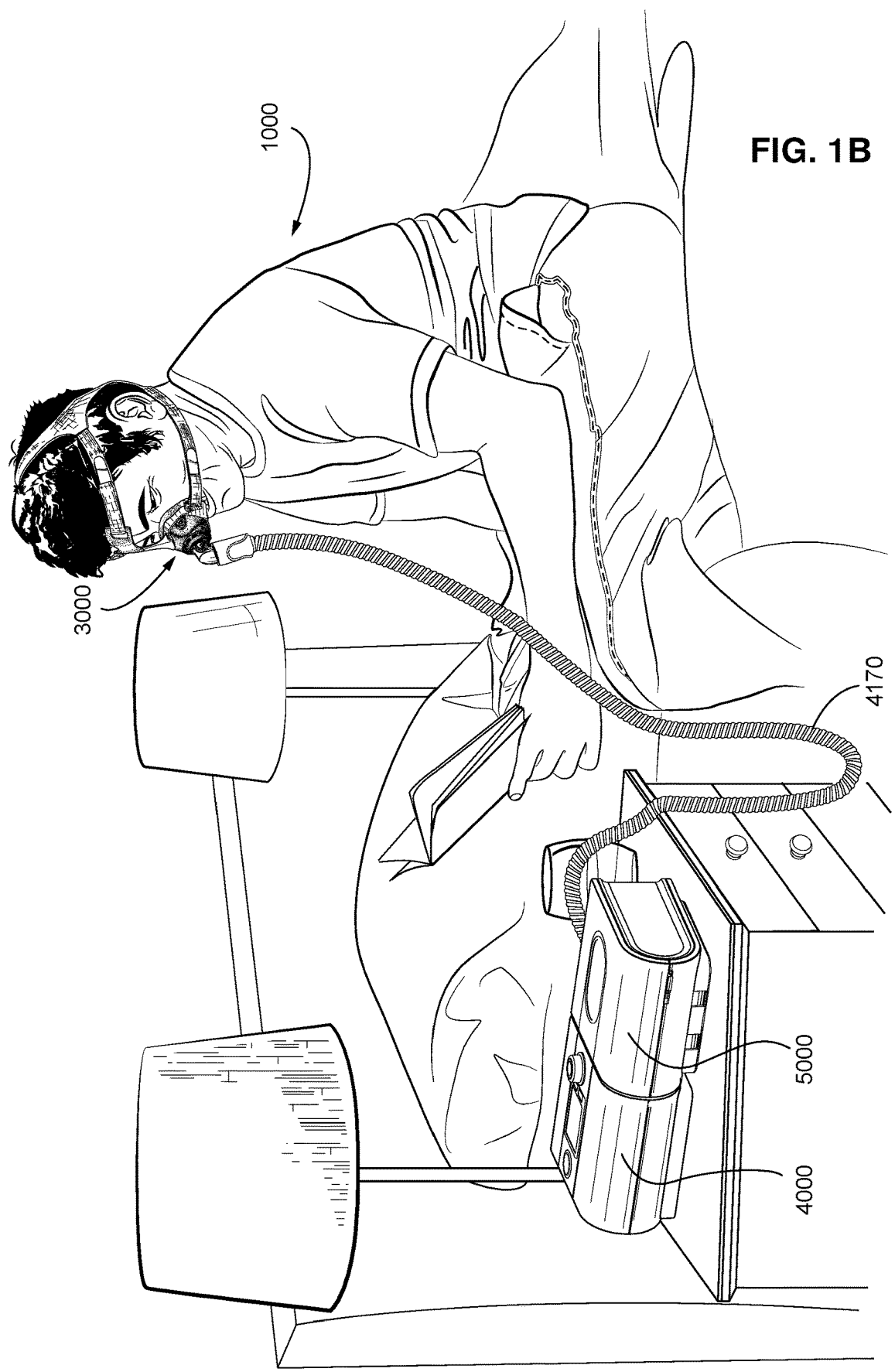
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
Figure 1C:
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 2A:
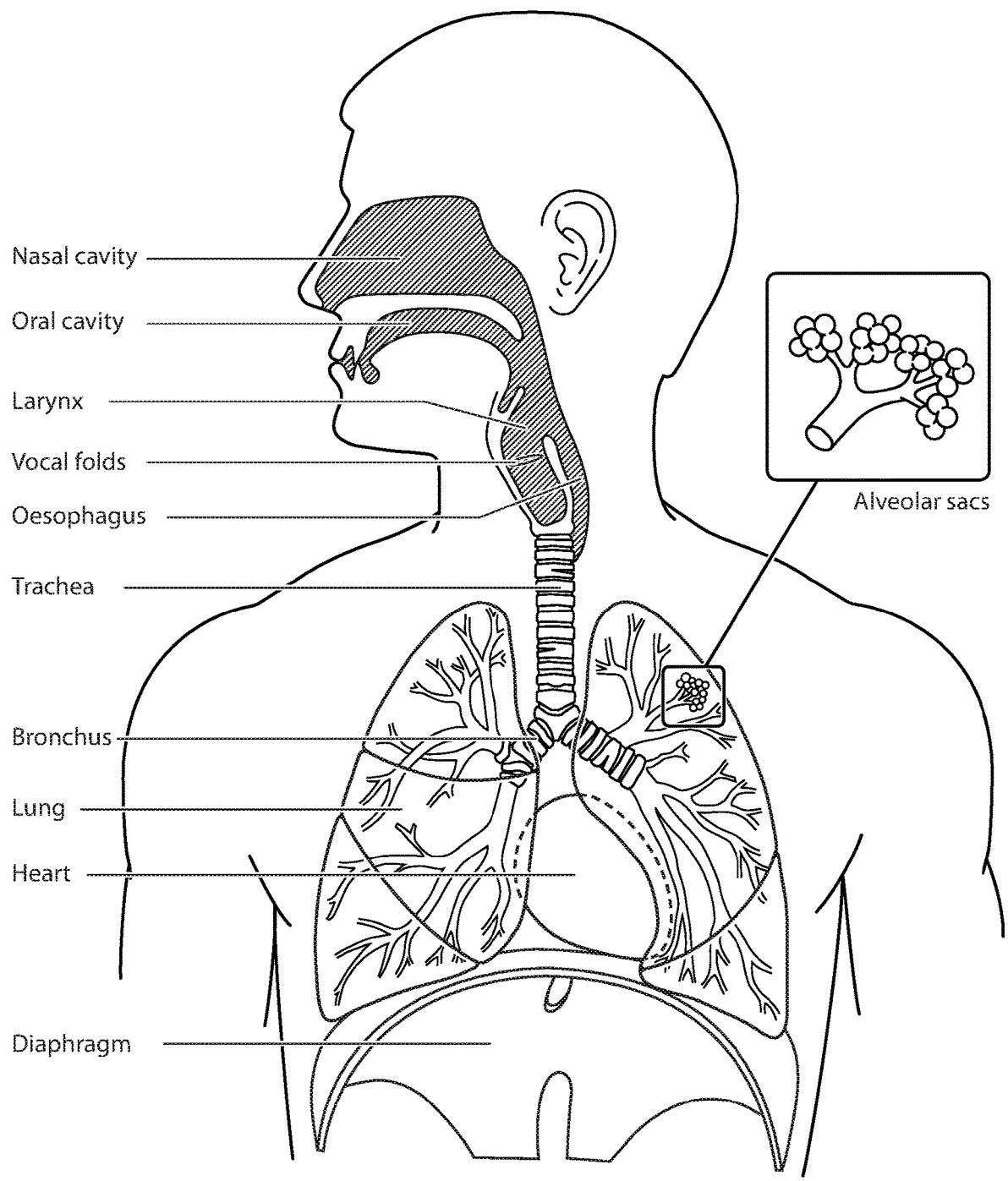

FIG. 2A shows an overview of a human respiratory system including the nasal and oral cavities, the larynx, vocal folds, oesophagus, trachea, bronchus, lung, alveolar sacs, heart and diaphragm.

Figure 2B:
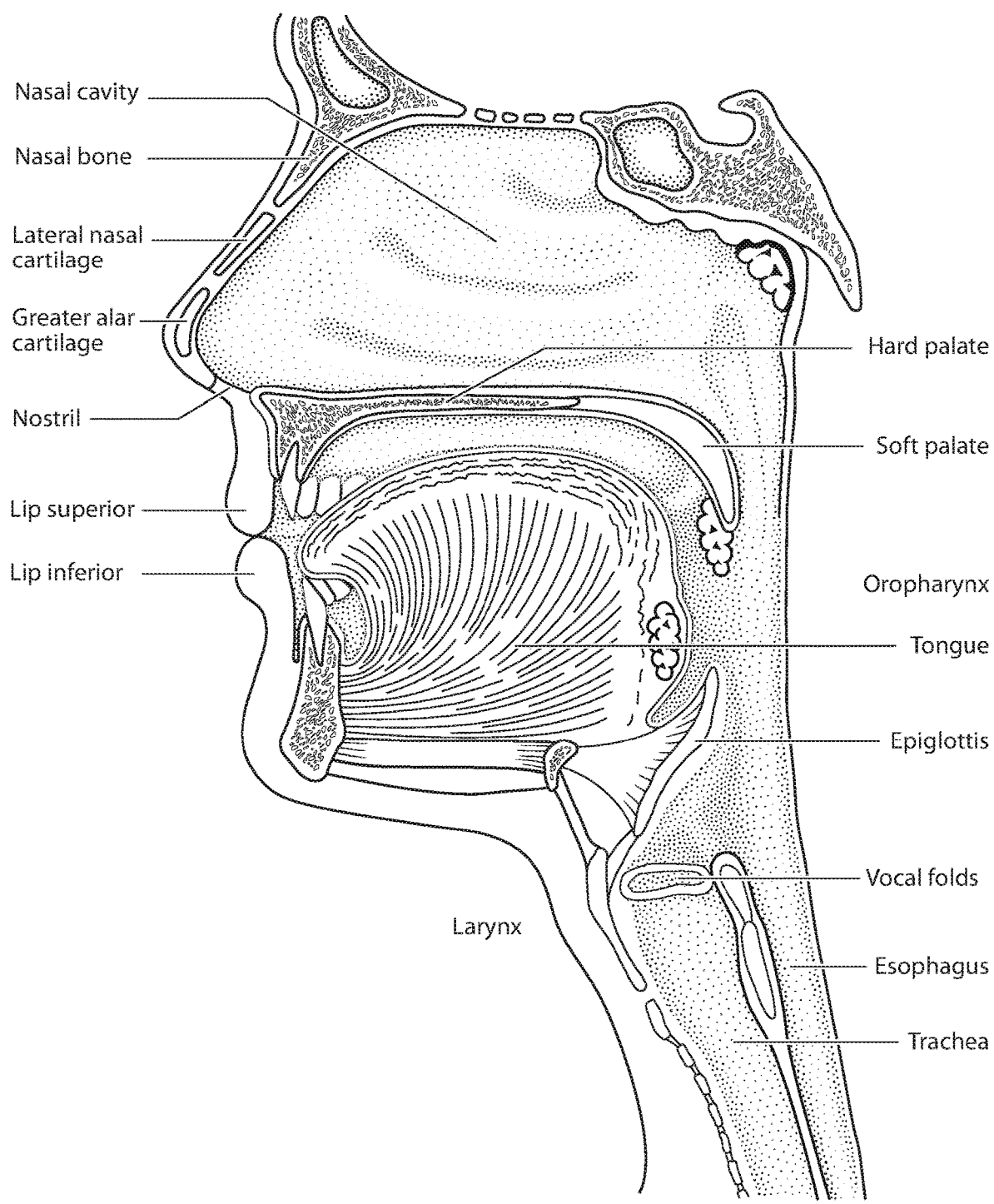

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
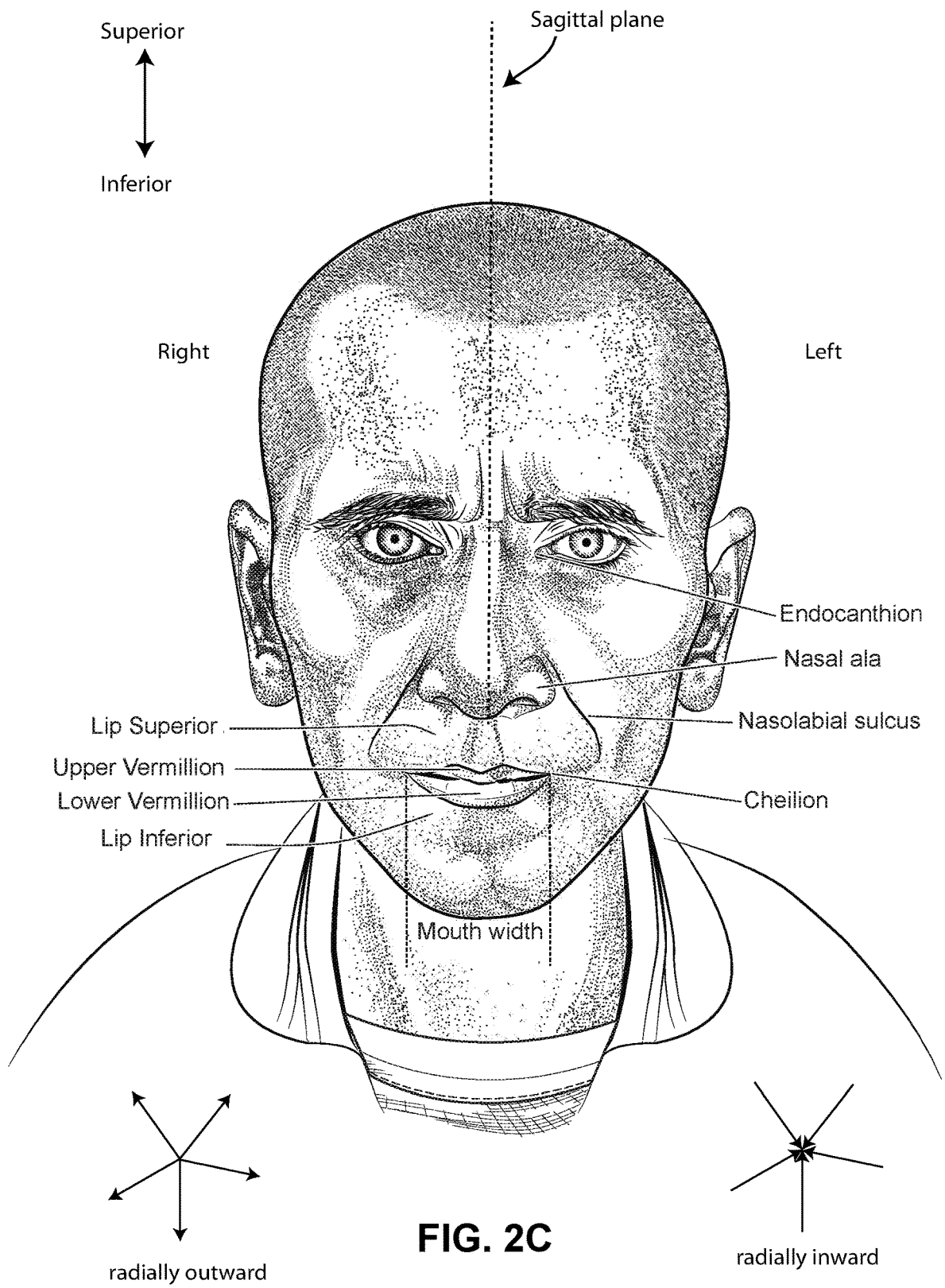

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
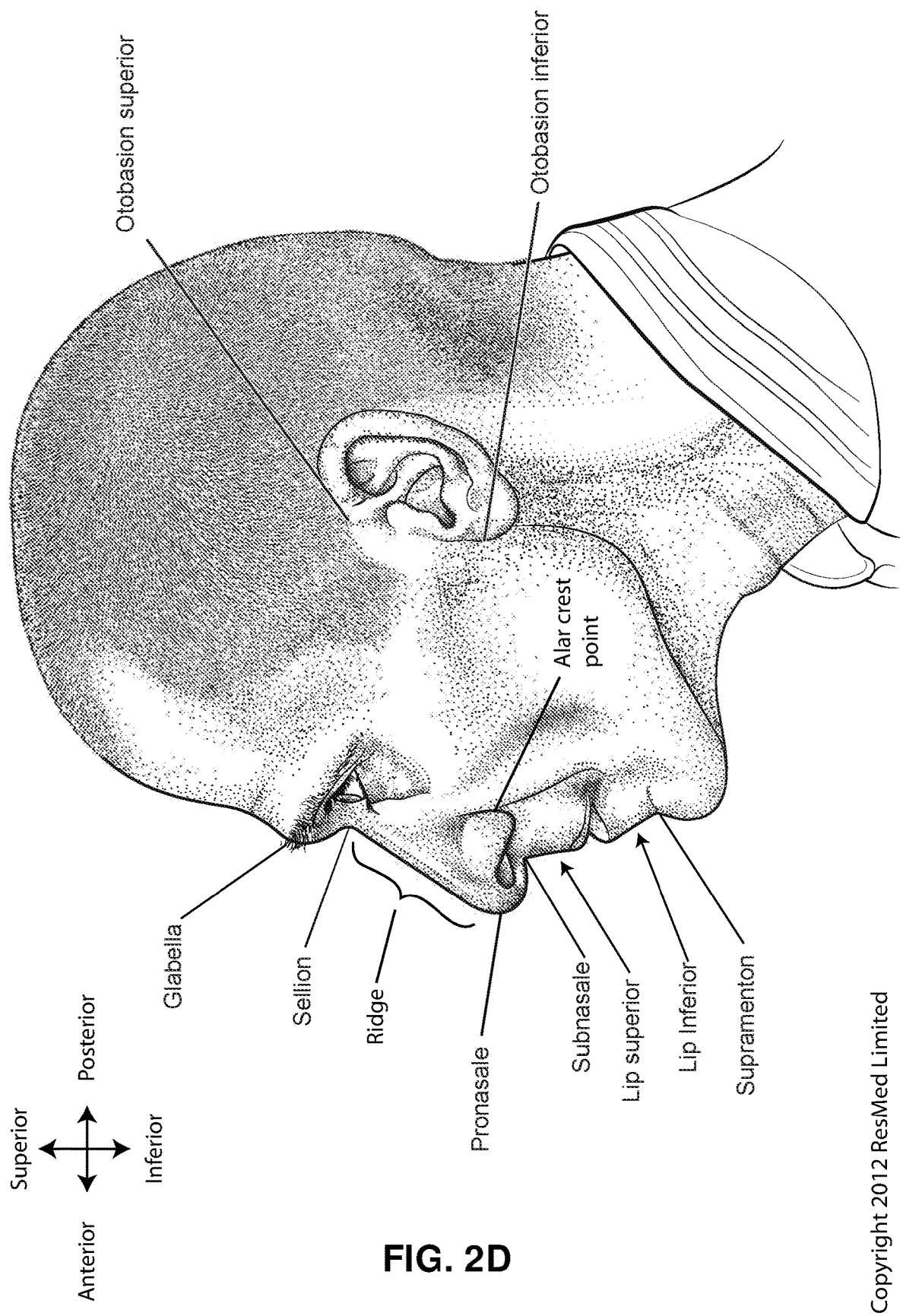

FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
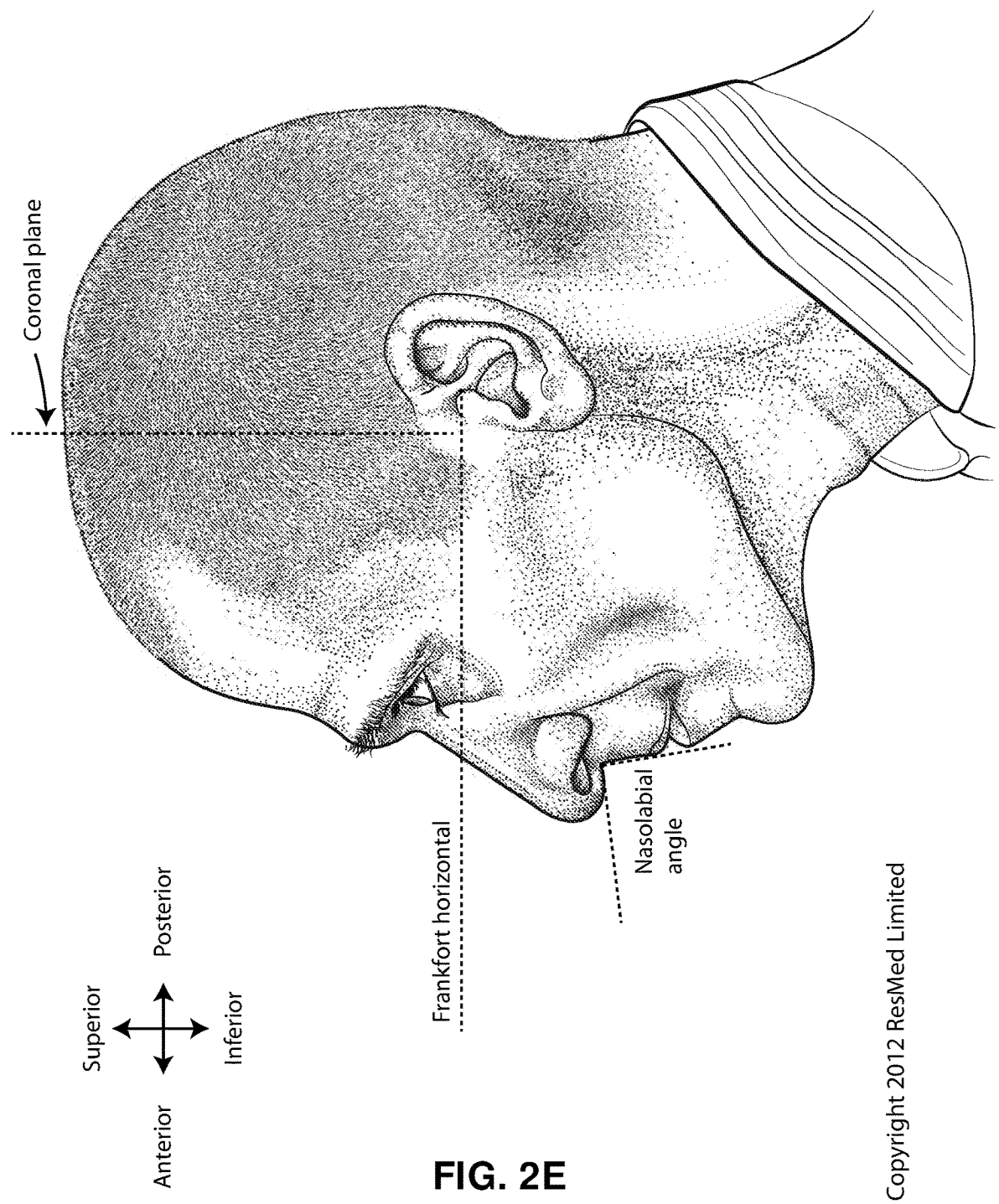

FIG. 2E is a further side view of a head. The approximate locations of the Frankfort horizontal and nasolabial angle are indicated. The coronal plane is also indicated.

Figure 2F:
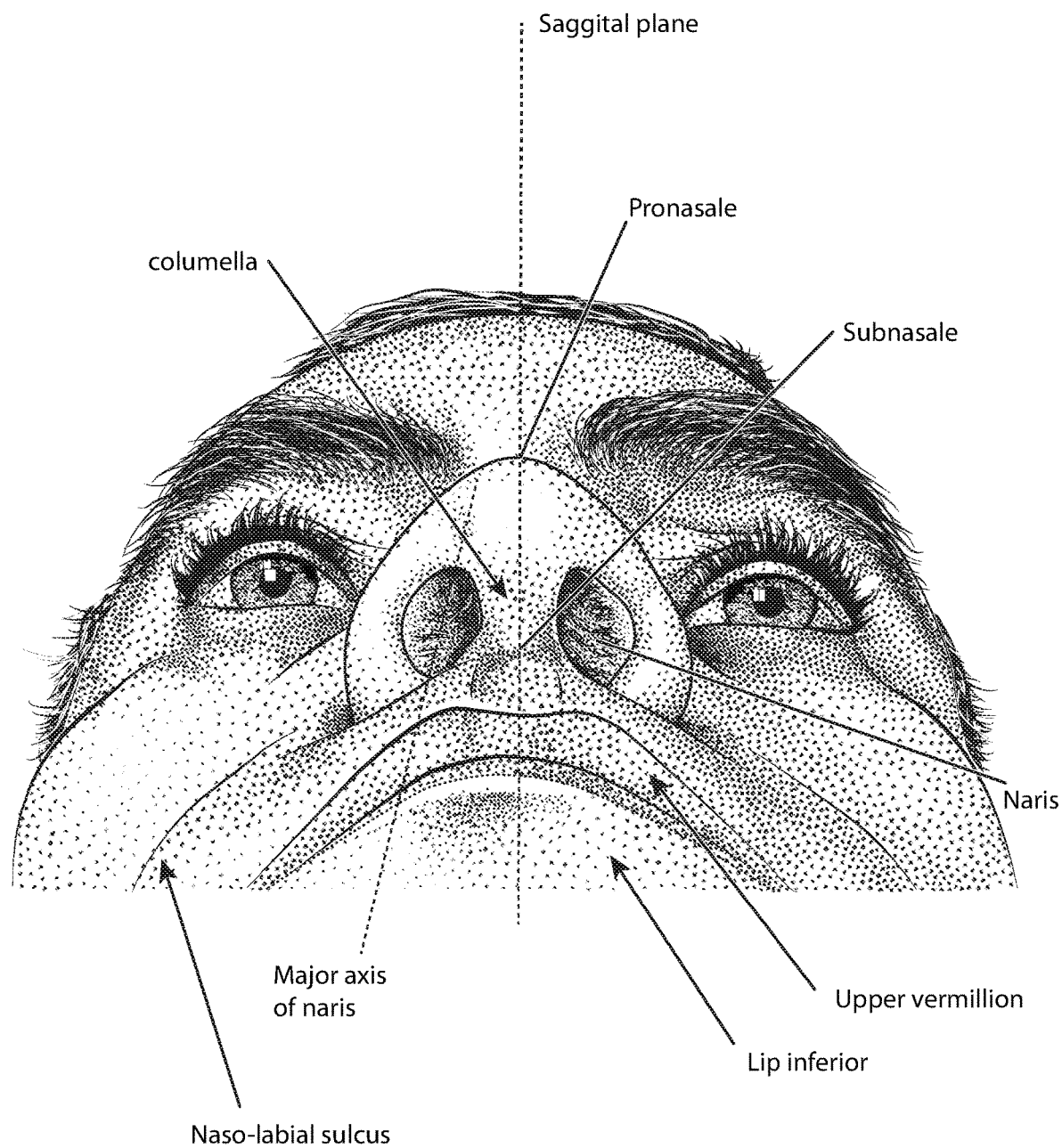

FIG. 2F shows a base view of a nose with several features identified including naso-labial sulcus, lip inferior, upper Vermilion, naris, subnasale, columella, pronasale, the major axis of a naris and the sagittal plane.

Figure 2I:
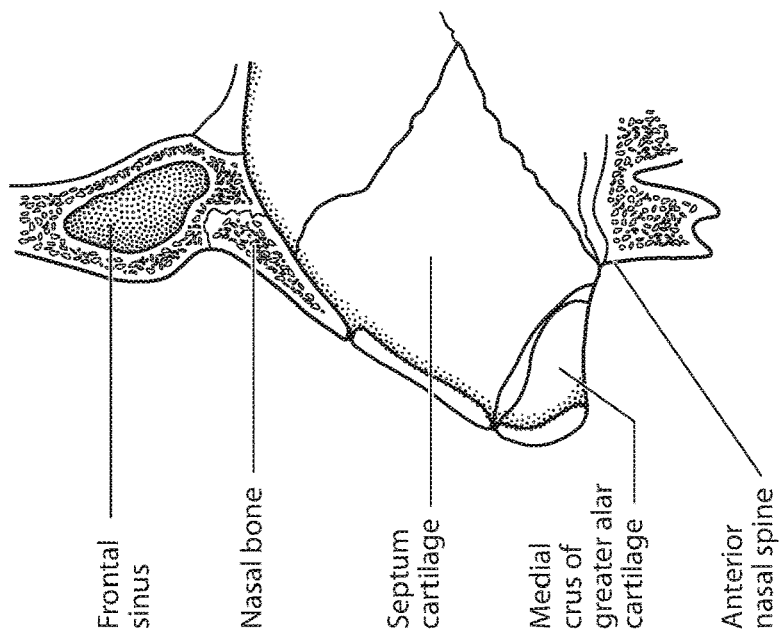
Figure 2H:
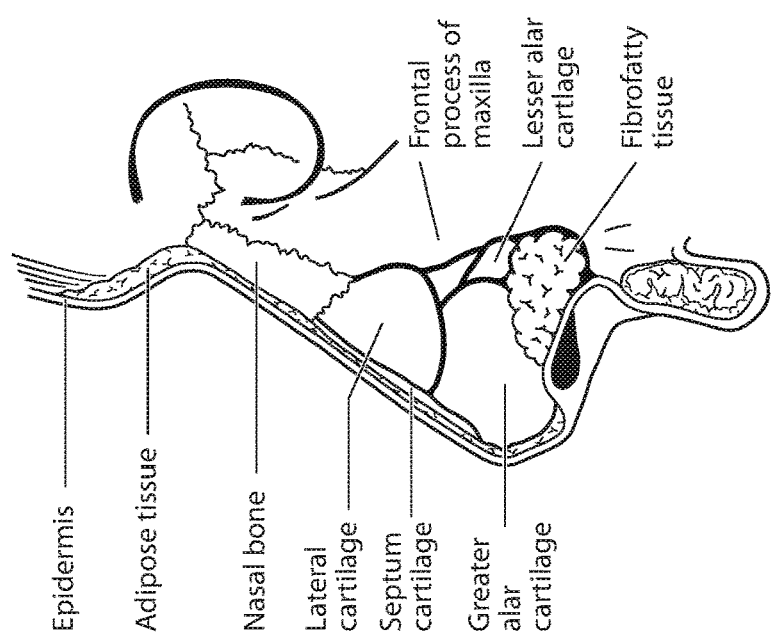
Figure 2G:

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from a sagittal plane, amongst other things showing the septum cartilage and medial crus of greater alar cartilage.

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
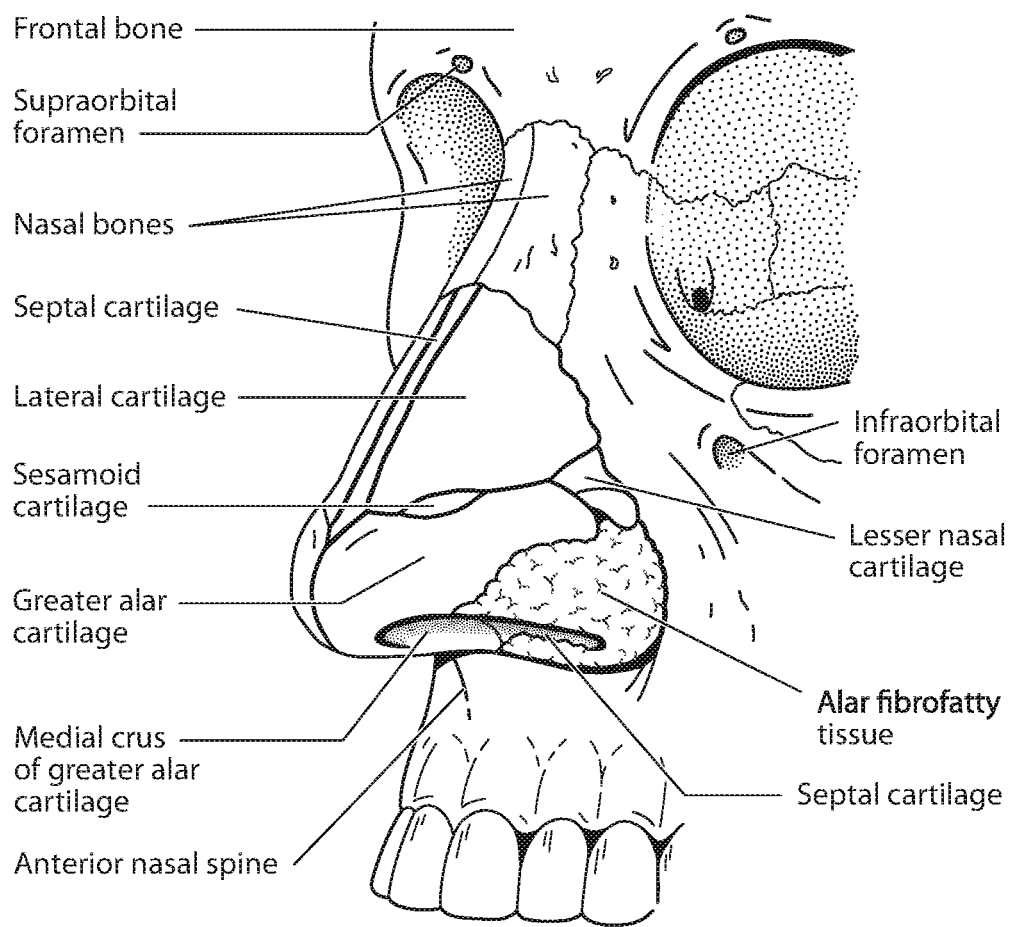

FIG. 2L shows an anterolateral view of a nose.

Patient Interface

Figure 3A:
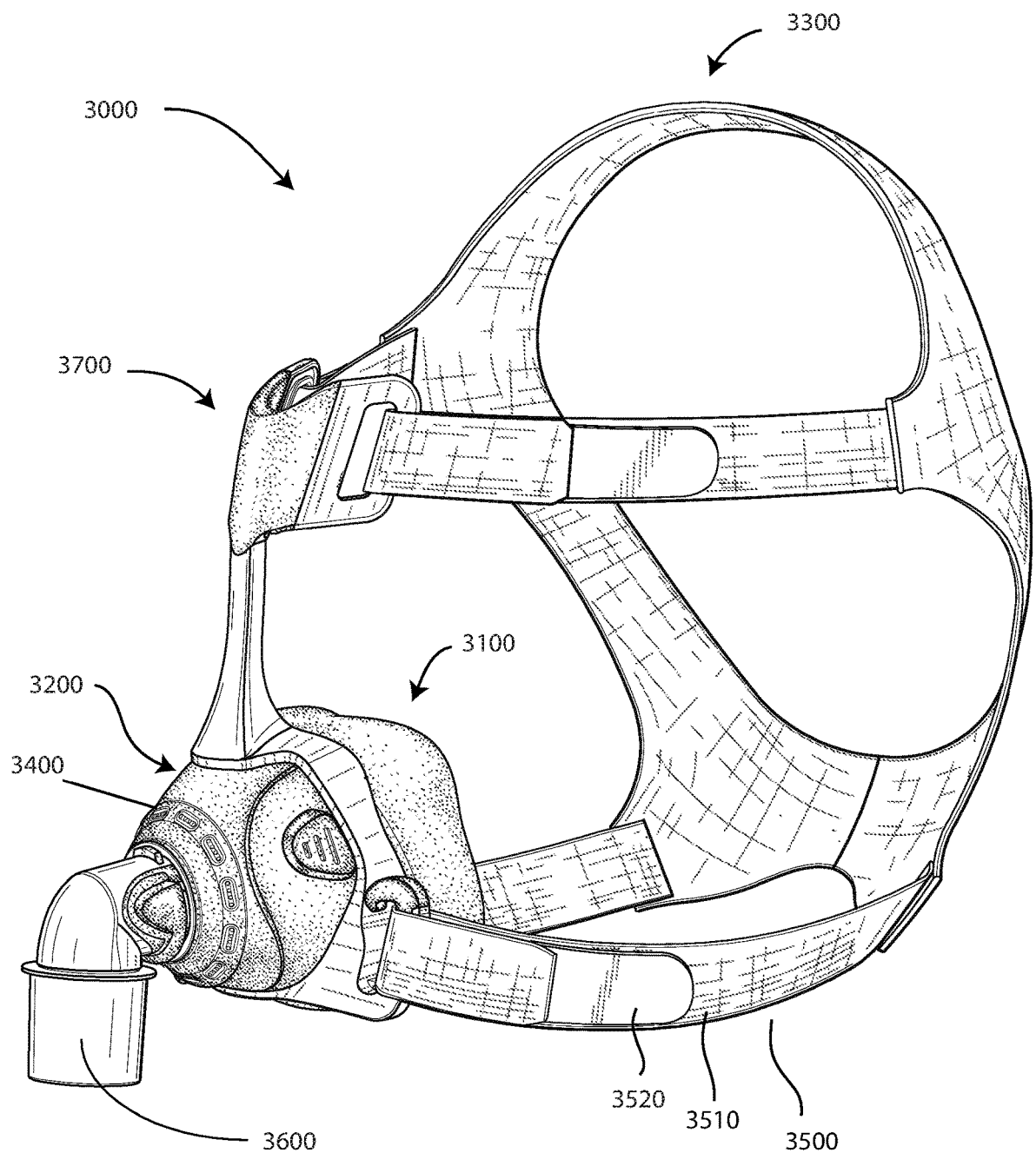

FIG. 3A shows a patient interface in the form of a nasal mask in accordance with one form of the present technology.

Figure 3B:
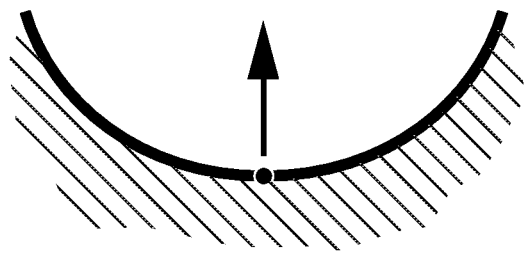

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
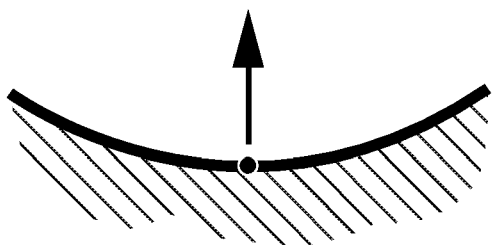

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
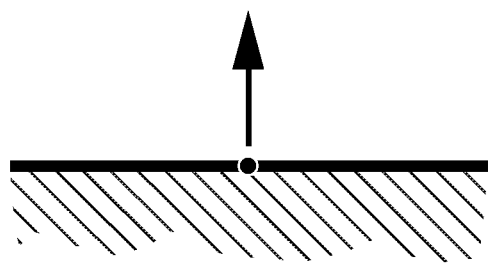

FIG. 3D shows a schematic of a cross-section through a structure at a point. An outward normal at the point is indicated. The curvature at the point has a value of zero.

Figure 3E:
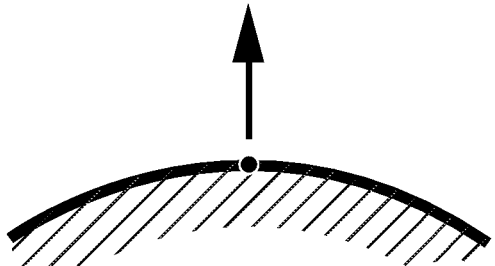

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
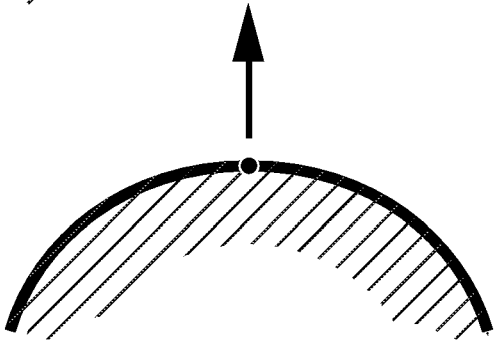

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
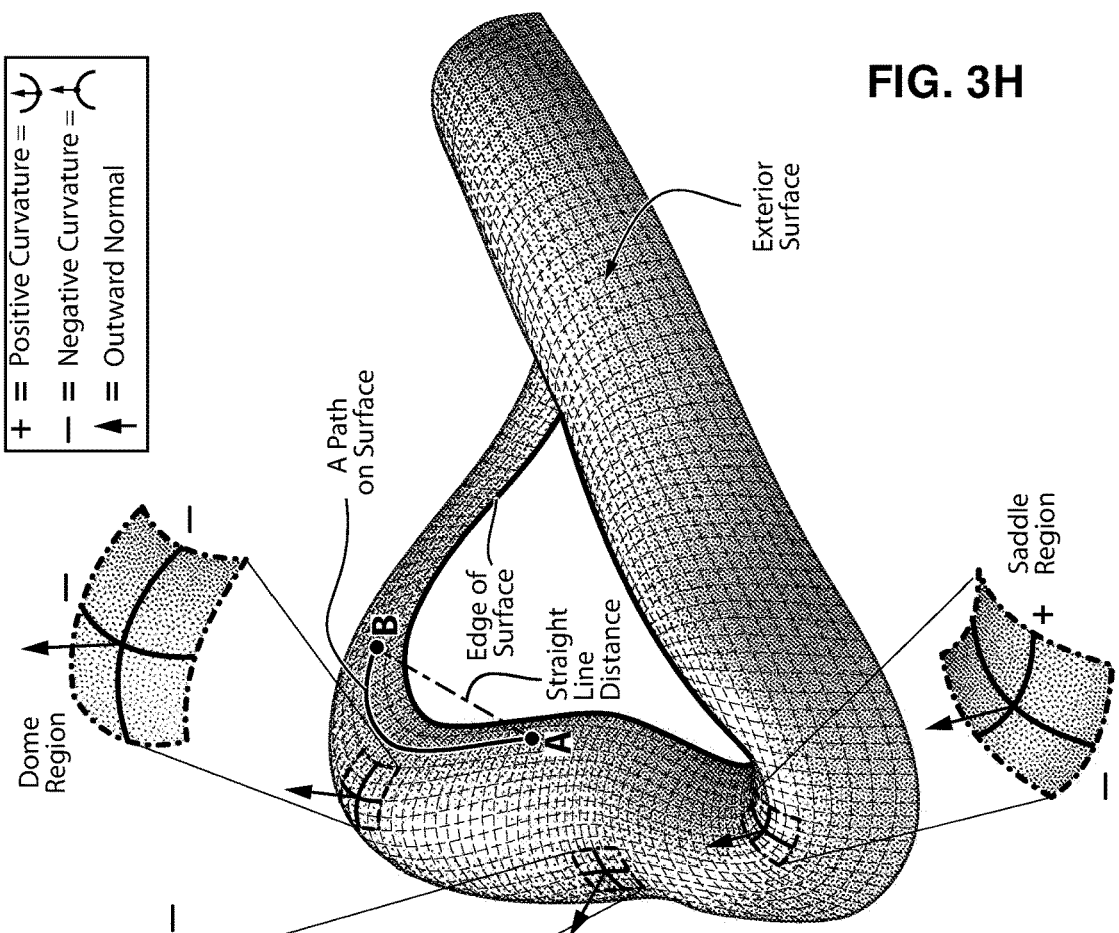
Figure 3G:
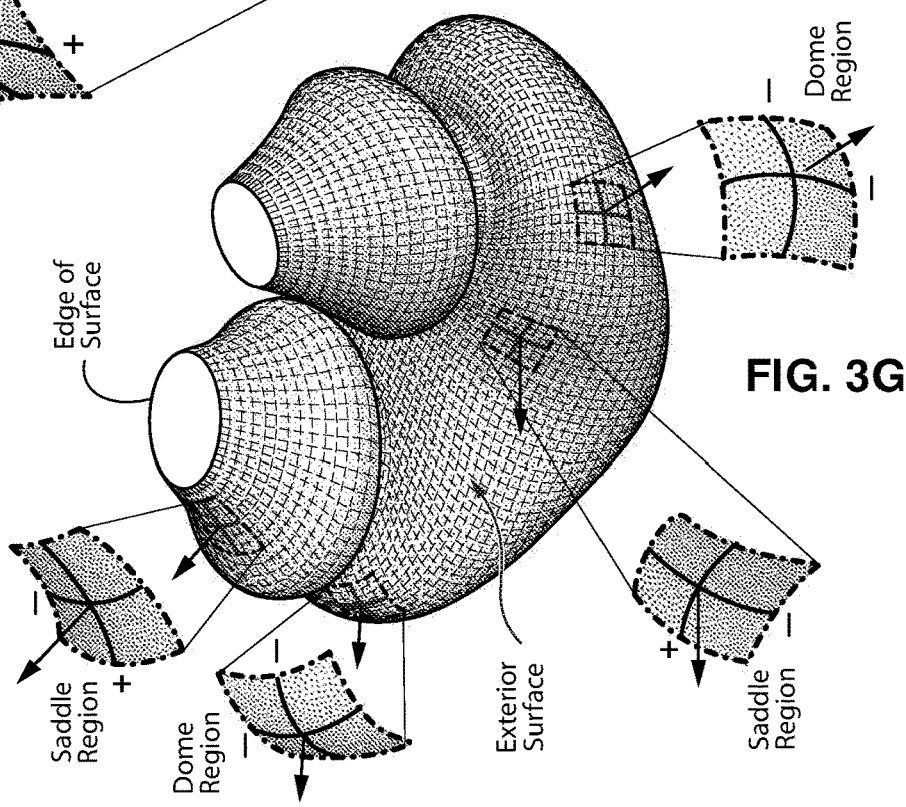

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Spacer Fabric

Figure 4A:
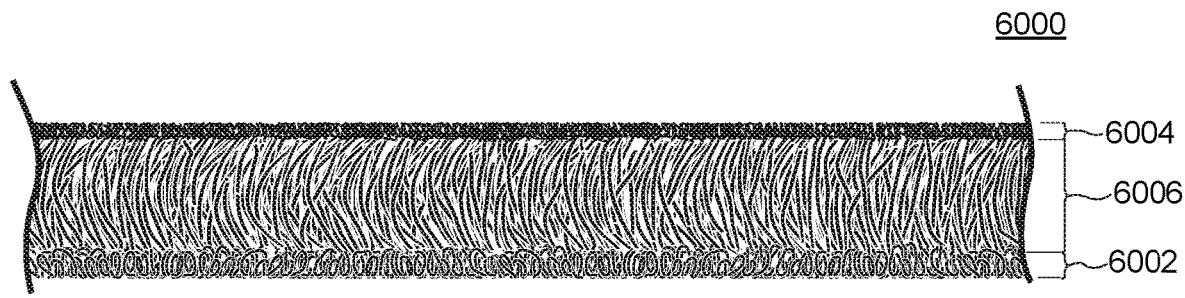

FIG. 4A shows a side or edge view of a first spacer fabric illustrating layers therein.

Figure 4B:
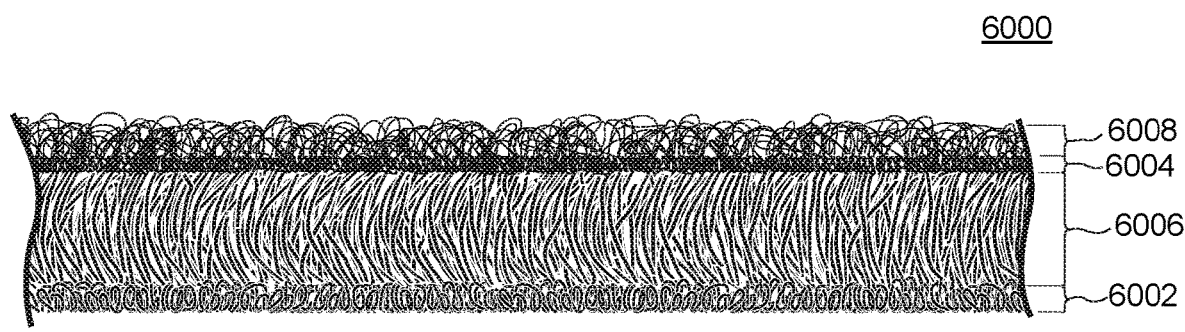

FIG. 4B shows a first side or edge view of a second spacer fabric illustrating layers therein.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

Seal-Forming Structure

In one form of the present technology, a seal-forming structure 3100 provides a seal-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange and a support flange. The sealing flange comprises a relatively thin member with a thickness of less than about 1 mm, for example about 0.25 mm to about 0.45 mm, that extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use. In use the sealing flange can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200.

Positioning and Stabilising Structure

The seal-forming structure 3100 of the patient interface 3000 of the present technology may be held in sealing position in use by the positioning and stabilising structure 3300 (illustrated as headgear).

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 comprises a strap constructed from a laminate of a fabric patient-contacting layer, a foam inner layer and a fabric outer layer. The laminate may be flame laminated. In one form, the foam is porous to allow moisture, (e.g., sweat), to pass through the strap. In one form, the fabric outer layer comprises loop material 3510 to engage with a hook material 3520.

In certain forms of the present technology, a positioning and stabilising structure 3300 comprises a strap that is extensible, e.g. resiliently extensible. For example the strap may be configured in use to be in tension, and to direct a force to draw a cushion into sealing contact with a portion of a patient's face. In an example the strap may be configured as a tie.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In one form of the present technology, the positioning and stabilising structure 3300 may include portions, such as a strap 3500, formed from a spacer fabric 6000 as illustrated in FIGS. 4A and 4B. Except as noted below, the entire positioning and stabilising structure 3300 may be formed from spacer fabric 6000. Spacer fabric 6000 may also be used in combination with the laminate structure described above.

The spacer fabric 6000 includes a first fabric layer 6002, a second fabric layer 6004 and a central fabric layer 6006. These three layers may be warp/weft knitted together, for example, by a warp knitting Raschel machine, warp-knit spacer machine, or circular knitting machine. The spacer fabric 6000 is porous and/or open celled, which provides benefits such as allowing the spacer fabric 6000 to breath, to be easily washed and to be faster to dry. A porous structure may enable the strap 3500 be washed more thoroughly and faster, as dirt and other foreign contaminants can be washed out faster and more is washed out without as much agitation compared to a conventional flame laminated headgear strap with a comparable amount of foreign contaminants.

The first fabric layer 6002 may be hydrophilic. If, for example, a hydrophilic layer is against the patient's skin, the hydrophilic material may wick away moisture, which may also provide cooling or a cooling sensation. The second fabric layer 6004 may be hygroscopic. This may aid the wicking effect of a hydrophilic layer. Alternatively or in addition, portions of the first fabric layer 6002 may be omitted to expose the central fabric layer. This may be advantageous if increased airflow, faster drying and/or reduced weight is desirable.

The central fabric layer 6006 may be made from a single filament or multiple filaments, for example, a single yarn or multiple yarns. This may allow for the central fabric layer 6006 to be spacer yarn or pile fabric, either of which may aid in transporting heat and/or liquid away from the patient. As illustrated in FIGS. 4A and 4B, the fibres of the central fabric layer 6006 extend from the first fabric layer 6002 to the second fabric layer 6004. Alternatively, the fibres of the central fabric layer 6006 are transverse to both the first fabric layer 6002 and the second fabric layer 6004 between the boundaries of those layers and thus may be considered to be oriented in a column-like fashion. With this configuration, the central fabric layer 6006 spaces the first fabric layer 6002 from the second fabric layer 6004 and the three layers together in this fashion may also be referred to as a 3D spacer fabric.

The spacer fabric 6002 may be elastic along a length of a strap. For example, any of the various straps illustrated in FIG. 3A may be elastic along the length (e.g., longest) dimension and may be inelastic, or less elastic, along the width or thickness.

Use of spacer fabric 6000 may differentiate over known straps and/or positioning and stabilising structures through the omission of foam. When foam is compressed, for example, when a patient sleeps on their side and the headgear is pressed against the patient's cheek, the foam does not compress beyond a certain point. In contrast, when compression force is applied to the spacer fabric 6000, the central fabric layer 6006 may collapse, which may result in the spacer fabric 6000 forming a very thin structure. This may improve comfort for the patient when they are sleeping on their side. Spacer fabric 6000 also separates compression strength from tensile strength in contrast to foam which have both strength properties linked to each other. The spacer fabric 6000 may further differentiate over straps in known positioning and stabilising structures in that the straps can be formed seamlessly. Thus the three-dimensional shape illustrated in FIG. 3A may be manufactured without the illustrated seams. Known positioning and stabilising structures may be flame laminated together, which could also result in a seam between the laminated layers but can be avoided using spacer fabric 6000. Flame lamination may also result in a structure that is subject to cracking when stretched, which can also be avoided using spacer fabric 6000. The positioning and stabilising structure 3300 may thus be fabricated without flame laminating and/or without glue laminating layers together.

Known positioning and stabilising structures may comprise a hollow strap which may receive the insertion of a rigidiser arm. A hollow strap without a rigidiser arm inserted may be prone to twisting and folding. If this occurs during therapy, it may be uncomfortable for the patient. A rigidiser may be inserted into the central fabric layer 6006, pushing fibres out of the way. Such a rigidiser may be used to provide a direction or vector in which the spacer fabric 6000 is intended to stretch in use. For example, it may be advantageous to have such a vector between the patient's eyes and ears. Alternatively, a rigidiser may be used to prevent stretching in a location of the positioning and stabilising structure 3300 where elasticity is not desirable or should be limited.

The first fabric layer 6002 may be smooth to the touch and/or have a soft appearance. This may be suitable for contact with a patient's skin. The first fabric layer 6002 may be a mesh.

The second fabric layer 6004 may be smooth to the touch and/or breathable. This may be suitable for a surface facing away from the patient because, for example, being breathable may allow entrained moisture (such as perspiration) to wick away from the patient and evaporate.

One or any combination of the first fabric layer 6002, the second fabric layer 6004, the third fabric layer 6008 (discussed below) and the central fabric layer 6006 may be fabricated by 3D knitting (i.e. three-dimensional knitting) or more specifically by warp knitting. Warp knitting is a method of knitting where the fibre, such as yarn, zigzags along the length of the fabric. In warp knitting a number of separate strands of fibre is equal to a number of stitches in a row and results in columns of knitting rather than a single row. By way of comparison, knitting across the width of fabric is called weft knitting.

Known types of warp knitting include Tricot, Milanese knit, Raschel knit, stitch-bonding and extended stitch bonding.

Stitch bonding includes layers of threads and fabric being joined together with a knitting thread. This creates a layered structure. The layered structure is created through a warp-knitting thread system that is fixed on the reverse side of the fabric with a sinker loop, and a weft thread layer. A needle with the warp thread passes through the material, which requires the warp and knitting threads to be moving both parallel and perpendicular to the vertical/warp direction. Stitch bonding is a method that can be used to warp/weft knit fabric together.

In extended stitch-bonding, a compound needle that pierces the piles is shifted laterally according to yarn guides. This can avoid residual stress and improve tensile and impact strength.

Stitch bonding or extended stitch bonding may be used to create all of the layers of spacer fabric together, e.g., the first fabric layer 6002, the second fabric layer 6004, the central fabric layer 6006 and the third fabric layer 6008 (discussed below). Any knitting type that can join layers together may be used.

The central fabric layer 6006 may be formed from or include yarn, e.g., a yarn layer. The yarn may include cotton yarn, polyester yarn or combinations thereof. The yarn may be fully cotton, partially cotton, fully polyester, partially polyester, nylon, silicone, elastane and/or polypropylene. The central fabric layer 6006 may include a predetermined number of yarns per square centimetre to provide a predetermined amount of elasticity and flexibility to the positioning and stabilising structure. The yarns making up the central fabric layer 6006 may have a predetermined thickness and/or predetermined height to provide a predetermined amount of elasticity and flexibility to the positioning and stabilising structure.

FIG. 4B differs from FIG. 4A in that a third fabric layer 6008 is illustrated. The third fabric layer 6008 may be an unbroken loop layer (UBL) or a mesh layer, which may be suitable for mating and/or fastening with a hook layer (e.g., hook material 3520) of a hook and loop fastener. By including an unbroken loop layer or a mesh layer as the third fabric layer 6008, the spacer fabric 6000 may integrally form the loop half of a hook and loop fastener. The loop material 3510 may be the third fabric layer 6008. The hook material 3520 may need to be attached to the spacer fabric 6000 and/or positioning and stabilising structure 3300 by suitable fastening methods such as stitching, gluing, etc.

The spacer fabric may range in thickness from 2.0-6.0 mm, range in compression strength from 5-25 kilopascals, and range in elongation from 0.1%-20% with a 10 Newtons force applied. For example, in one form (e.g., a thick, low-stretch spacer fabric), the spacer fabric 6000 may have a thickness of 4.0-6.0 mm, a compression strength of 15-25 kilopascals, and an elongation of 1%-5% with a 10 Newtons force applied. In another form (e.g., thick, high-stretch spacer fabric), the spacer fabric 6000 may have a thickness of 4.0-6.0 mm, a compression strength of 15-25 kilopascals, and an elongation of 10%-20% with a 10 Newtons force applied. In yet another form (e.g., thin, medium-stretch spacer fabric), the spacer fabric 6000 may have a thickness of 2.0-4.0 mm, a compression strength of 5-20 kilopascals, and an elongation of 6%-10% with a 10 Newtons force applied. In another form, the combination of the first fabric layer 6002, second fabric layer 6004 and central fabric layer 6006 together may have 10% to 15% elongation when a 10 Newtons force is applied. In yet another form, the combination of the first fabric layer 6002, second fabric layer 6004 and central fabric layer 6006 together may have 10% to 30% elongation when a 2 Newtons force is applied. Spacer fabric with little or no stretch (e.g., 0.1% with 10 Newtons force applied) may be suitable for portions of the positioning and stabilising structure where stretch may not be desirable, for example, a strap on the crown of a patient's head.

Any of the various thicknesses of the spacer fabric 6000 may include the third fabric layer 6008. For example, a spacer fabric 6000 with a thickness of 2.0-4.0 mm may include the third fabric layer 6008.

By fabricating the spacer fabric 6000 using the 3D knitting techniques described above, the spacer fabric 6000 may seamlessly transition between these properties. For example, the spacer fabric could transition from a 2.0 mm thickness to a 6.0 mm thickness without a seam. The change in thickness may also result in proportional changes in the compression strength and elongation.

The spacer fabric 6000 may also be separately fabricated and joined together, e.g., by stitching or gluing, to utilize different combinations of properties above. For example, a spacer fabric with 2.0-4.0 mm thickness and the third fabric layer 6008 (e.g., thin, medium-stretch spacer fabric) could be fastened to a spacer fabric with 4.0-6.0 mm thickness (e.g., thick, high-stretch spacer fabric) so that part of the positioning and stabilising structure 3300 has unbroken loops where medium elongation (e.g., 6%-10%) is desired and omits unbroken loops where relatively high elongation (e.g., 10%-20%) is desired.

Of course, any combination of the various types of spacer fabric 6000 may be joined, either using conventional connection techniques like stitching and gluing or using knitting techniques, so that the properties are controlled as desired based upon their relative location in the positioning and stabilising structure 3300. Thus different strap portions of the positioning and stabilising structure 3300 can be formed with a first fabric layer 6002, a second fabric layer 6004 and a central fabric layer 6006 while achieving differing structural properties (such as thickness, elongation and compression strength).

3D knitting may provide a more durable headgear. For example, 3D knitting processes may produce a material that will not run even if cut.

The edge of the spacer fabric 6000 may be closed while it is manufactured. A closed and rounded edge is comfortable for a patient as it may avoid red marks on the patient's skin.

The spacer fabric 6000 may result in a positioning and stabilising structure and/or strap that is more breathable and lighter than a comparable flame laminated structure. The ability to knit to shape (e.g., 3D knitting) can reduce cost because, for example, scrap is eliminated as comparted to materials that must be cut to shape from a sheet of material. The shape of the positioning and stabilising structure of FIG. 3A can be achieved so that the straps and open spaces are initially formed by the knit to shape process. The ability to knit to shape also allows for controlled change of properties as described above.

The spacer fabric 6000 may be easier to clean than other types of material used for a positioning and stabilising structure. A bioburden cleaning confidence test was performed per ISO 15883-5 (2005) on a strip of spacer fabric as disclosed herein and on a strip of Breath-O-Prene. The result of the test was that spacer fabric displayed superior cleaning characteristics versus the Breath-O-Prene.

Vent

In one form, the patient interface 3000 includes a vent 3400 constructed and arranged to allow for the washout of exhaled gases, e.g. carbon dioxide.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

Decoupling Structure(s)

In one form the patient interface 3000 includes at least one decoupling structure, for example, a swivel or a ball and socket.

Connection Port

Connection port 3600 allows for connection to the air circuit 4170.

Forehead Support

In one form, the patient interface 3000 includes a forehead support 3700.

Anti-Asphyxia Valve

In one form, the patient interface 3000 includes an anti-asphyxia valve.

Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

GLOSSARY

For the purposes of the present technology disclosure, in certain forms of the present technology, one or more of the following definitions may apply. In other forms of the present technology, alternative definitions may apply.

General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system. Respiratory flow rate, Qr, is the flow rate of air that is received into the patient's respiratory system.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory disease.

Pressure: Force per unit area. Pressure may be expressed in a range of units, including $cmH_2O$, $g$-$f/cm^2$ and hectopascal. 1 $cmH_2O$ is equal to 1 $g$-$f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a typically transparent thermoplastic polymer of Bisphenol-A Carbonate.

Mechanical Properties

Resilience: Ability of a material to absorb energy when deformed elastically and to release the energy upon unloading.

'Resilient': Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

'Floppy' structure or component: A structure or component that will change shape, e.g. bend, when caused to support its own weight, within a relatively short period of time such as 1 second.

'Rigid' structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Hypopnea: Preferably, a hypopnea will be taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal flow rate.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

Ventilation

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Anatomy

Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow directs an axis of flow of air to change direction through an angle. In one form, the angle may be approximately 90 degrees. In another form, the angle may be less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilising structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie: A tie will be taken to be a structural component designed to resist tension.

Vent: (noun) the structure that allows a flow of air from an interior of the mask, or conduit, to ambient air to allow clinically effective washout of exhaled gases. For example, a clinically effective washout may involve a flow rate of about 10 litres per minute to about 100 litres per minute, depending on the mask design and treatment pressure.

Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a cushion structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

Space Curves

Space curves: Unlike a plane curve, a space curve does not necessarily lie in any particular plane. A space curve may be considered to be a one-dimensional piece of three-dimensional space. An imaginary person walking on a strand of the DNA helix walks along a space curve. FIG. 3I shows a right-hand helix. A typical human right ear comprises a right-hand helix. A typical human left ear comprises a left-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3J), or alternatively by a left-hand rule.

Osculating plane: The plane containing the unit tangent vector and the unit principal normal vector.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path).

With reference to the right-hand rule, a space curve turning towards the direction of the right-hand binormal may be considered as having a right-hand positive torsion (e.g. a right-hand helix). A space curve turning away from the direction of the right-hand binormal may be considered as having a right-hand negative torsion (e.g. a left-hand helix).

Equivalently, and with reference to a left-hand rule, a space curve turning towards the direction of the left-hand binormal may be considered as having a left-hand positive torsion (e.g. a left-hand helix). Hence left-hand positive is equivalent to right-hand negative.

Holes

A surface may have a one-dimensional hole, e.g. a hole bounded by a plane curve or by a space curve. Thin structures, e.g. a membrane with a hole, may be described as having a one-dimensional hole.

A structure may have a two-dimensional hole, e.g. a hole bounded by a surface. For example, an inflatable tyre has a two dimensional hole bounded by the inside surface of the tyre. In another example, a bladder with a cavity for air or gel could have a two-dimensional hole.

Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

REFERENCE SIGNS LIST 1000 patient
1100 bed partner
3000 patient interface
3100 seal—forming structure
3200 plenum chamber
3300 positioning and stabilising structure
3400 vent
3500 strap
3510 loop material
3520 hook material
3600 connection port
3700 forehead support
4000 RPT device
4170 air circuit
5000 humidifier
6000 spacer fabric
6002 first fabric layer
6004 second fabric layer
6006 central fabric layer
6008 third fabric layer

The invention claimed is:

1. A positioning and stabilising structure for a patient interface for delivery of a supply of pressurized air or breathable gas to a patient's airways, the positioning and stabilising structure comprising:
    a first spacer fabric section including:
        a first inner fabric layer;
        a first outer fabric layer;
        a first central fabric layer between the first inner fabric layer and the first outer fabric layer; and
        a connector fabric layer on the first outer fabric layer such that the first outer fabric layer is between the first central fabric layer and the connector fabric layer,
        wherein the first central fabric layer, the first inner fabric and the first outer fabric are warp/weft knitted together, and
        wherein the connector fabric layer comprises unbroken loops and is configured to fasten to hooks of a hook and loop fastener to enable length adjustment of the positioning and stabilising structure;
    a second spacer fabric section joined to the first spacer fabric section, the second spacer fabric section including:
        a second inner fabric layer;
        a second outer fabric layer;
        a second central fabric layer between the second inner fabric layer and the second outer fabric layer,
        wherein the second spacer fabric section does not include a layer of unbroken loops, and
        wherein the second central fabric layer, the second inner fabric layer and the second outer fabric layer are warp/weft knitted together, and
    wherein the first spacer fabric section has 6% to 10% elongation when a 10 Newtons force is applied, and
    wherein the second spacer fabric section has 10% to 20% elongation when a 10 Newtons force is applied.

2. The positioning and stabilising structure according to claim 1, wherein the first central fabric layer, the first inner fabric layer and the first outer fabric layer form a strap of the positioning and stabilising structure.

3. The positioning and stabilising structure according to claim 2, wherein the strap is porous.

4. The positioning and stabilising structure according to claim 2, wherein the strap is elastic at least along a length of the strap.

5. The positioning and stabilising structure according to claim 2, wherein the strap does not comprise foam.

6. The positioning and stabilising structure according to claim 1, wherein the first inner layer is hydrophilic.

7. The positioning and stabilising structure according to claim 1, wherein the first outer layer is hygroscopic.

8. The positioning and stabilising structure according to claim 1, wherein the first inner fabric layer, the first outer fabric layer and the first central fabric layer are made by warp knitting.

9. The positioning and stabilising structure according to claim 1, wherein the first central fabric layer is made by a 3D knitting machine.

10. The positioning and stabilising structure according to claim 1, wherein the first spacer fabric section is 2.0 mm to 6.0 mm thick.

11. The positioning and stabilising structure according to claim 10, wherein the first spacer fabric section is 6.0 mm thick.

12. The positioning and stabilising structure according to claim 10, wherein the first spacer fabric section is 4.0 mm thick.

13. The positioning and stabilising structure according to claim 1, wherein the first central fabric layer, the first inner fabric layer and the first outer fabric layer together have a compression strength that is 15 kilopascals to 25 kilopascals.

14. The positioning and stabilising structure according to claim 1, wherein the first spacer fabric section has a thickness of 2.0 mm to 4.0 mm, and the second spacer fabric section has a thickness of 4.0 mm to 6.0 mm.

15. The positioning and stabilising structure according to claim 1, wherein the second spacer fabric section has 10% to 15% elongation when a 10 Newtons force is applied.

16. The positioning and stabilising structure according to claim 1, wherein the first central fabric layer is a yarn layer.

17. The positioning and stabilising structure according to claim 16, wherein yarn of the yarn layer comprises cotton.

18. The positioning and stabilising structure according to claim 16, wherein yarn of the yarn layer comprises polyester.

* * * * *